US012056884B2

United States Patent
Shanmuganathan et al.

(10) Patent No.: US 12,056,884 B2
(45) Date of Patent: Aug. 6, 2024

(54) DETERMINING 3-D FACIAL INFORMATION OF A PATIENT FROM A 2-D FRONTAL IMAGE OF THE PATIENT

(71) Applicant: KONINKLIJKE PHILIPS N.V., Eindhoven (NL)

(72) Inventors: Praveen Kumar Pandian Shanmuganathan, Monroeville, PA (US); Richard Andrew Sofranko, Finleyville, PA (US); Anthony Vincent Startare, Belle Vernon, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 459 days.

(21) Appl. No.: 17/242,655

(22) Filed: Apr. 28, 2021

(65) Prior Publication Data

US 2021/0358144 A1 Nov. 18, 2021

Related U.S. Application Data

(60) Provisional application No. 63/025,822, filed on May 15, 2020.

(51) Int. Cl.
*G06T 7/00* (2017.01)
*A61M 16/06* (2006.01)
(Continued)

(52) U.S. Cl.
CPC .............. *G06T 7/50* (2017.01); *A61M 16/06* (2013.01); *G06N 3/04* (2013.01); *G06N 3/08* (2013.01);
(Continued)

(58) Field of Classification Search
CPC ... G06T 7/50; G06T 7/73; G06T 2207/10024; G06T 2207/20081; G06T 2207/20084; G06T 2207/30004; G06T 2207/30201; A61M 16/06; A61M 2016/0661; A61M 2205/3306; G06N 3/04; G06N 3/08; G06V 40/171; G06V 20/647
See application file for complete search history.

(56) References Cited

U.S. PATENT DOCUMENTS 7,904,193 B2 * 3/2011 Janbakhsh ............ A61M 16/06
700/118
10,650,564 B1 * 5/2020 Lin ..................... G06F 18/2413
(Continued)

OTHER PUBLICATIONS

International Search Report for PCT/EP2021/062241 filed May 8, 2021.
(Continued)

*Primary Examiner* — Ping Y Hsieh
(74) *Attorney, Agent, or Firm* — Michael W. Haas

(57) ABSTRACT

A method of identifying a particular mask for a patient for use in delivering a flow of breathing gas to the patient is carried out by first receiving a 2-D frontal image of the patient. Next, 3-D facial information of the patient is determined from the 2-D frontal image. At least some of the 3-D facial information is compared with dimensional information of a plurality of candidate masks. Finally, the particular mask for the patient is determined from a result of the comparison of the at least some of the 3-D facial information and the dimensional information of the plurality of candidate masks.

12 Claims, 8 Drawing Sheets

(51) Int. Cl.
  *G06N 3/04* (2023.01)
  *G06N 3/08* (2023.01)
  *G06T 7/50* (2017.01)
  *G06T 7/73* (2017.01)

(52) U.S. Cl.
  CPC ....... *G06T 7/73* (2017.01); *A61M 2016/0661* (2013.01); *A61M 2205/3306* (2013.01); *G06T 2207/10024* (2013.01); *G06T 2207/20081* (2013.01); *G06T 2207/20084* (2013.01); *G06T 2207/30004* (2013.01); *G06T 2207/30201* (2013.01)

(56) References Cited

U.S. PATENT DOCUMENTS

2019/0099573 A1* 4/2019 Pandian Shanmuganathan .......... A61M 16/0616
2021/0386383 A1* 12/2021 McDuff ............... A61B 5/0205

OTHER PUBLICATIONS

Zeng, X. et al., "DF2 Net: A Dense-Fine-FInder Network fro Detailed 3D Face Reconstruction". 2019 IEEE/CVF International Conference on Computer Vision (ICCV). DOI 10.1109/ICCV.2019.00240.

* cited by examiner

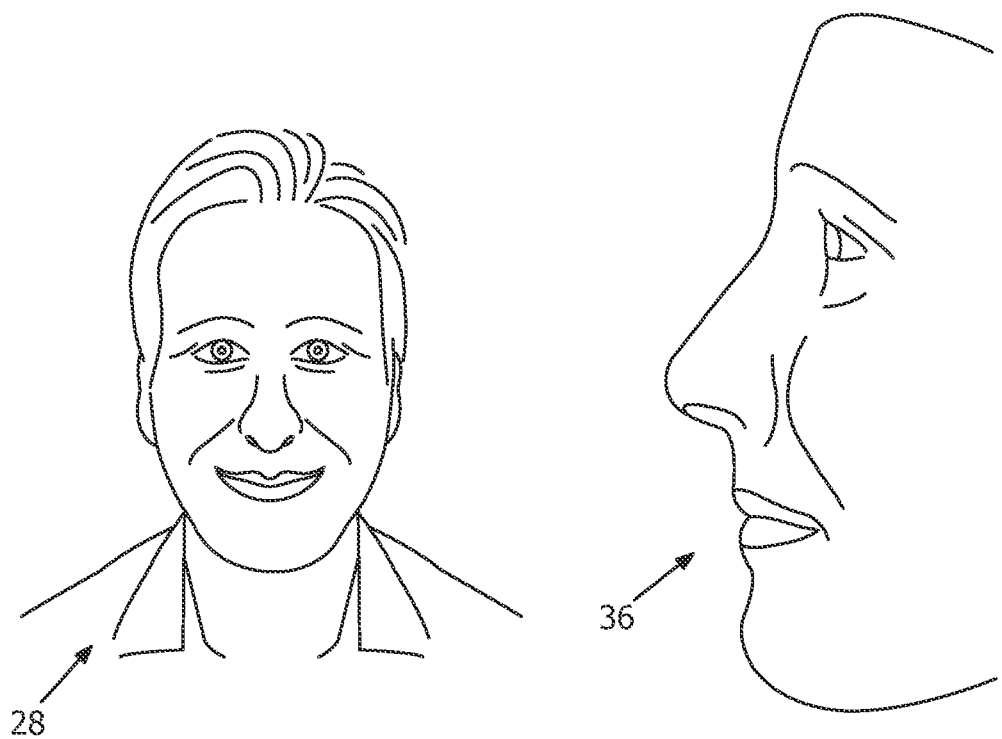
FIG. 6A
FIG. 6C
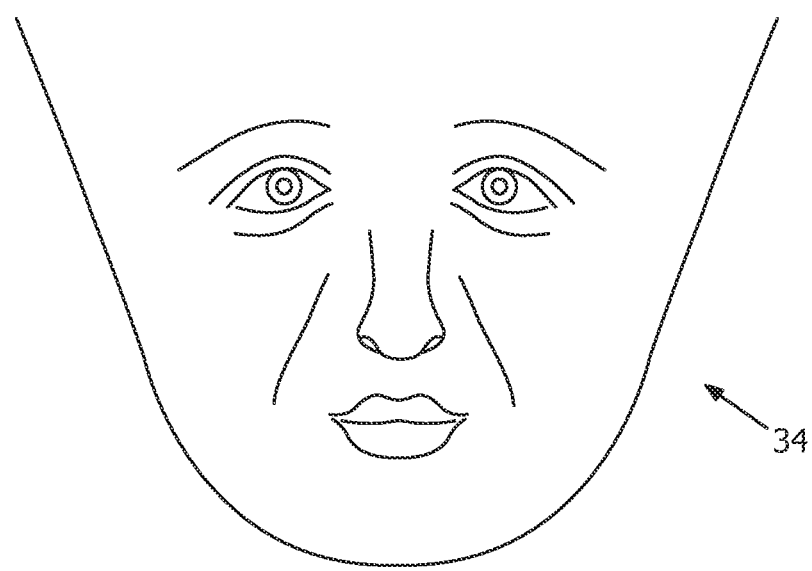
FIG. 6B

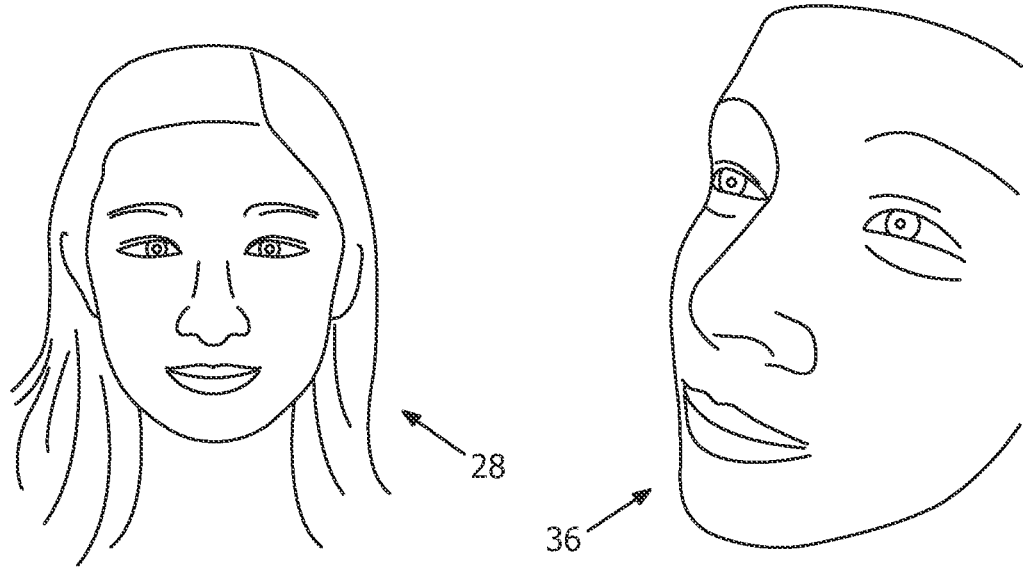
FIG. 7A
FIG. 7C
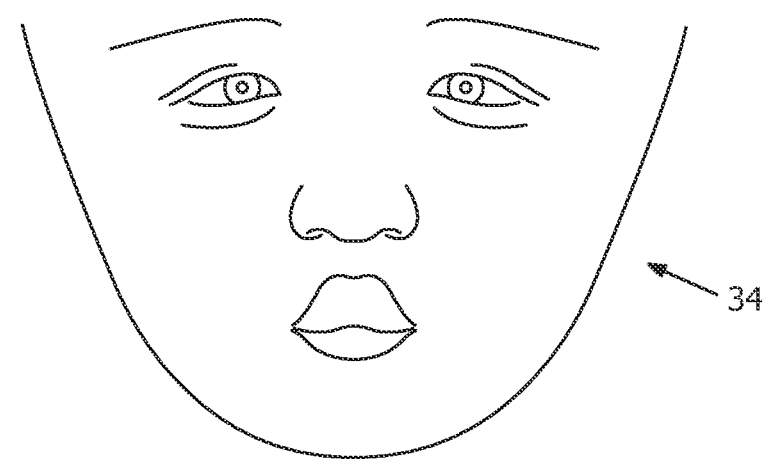
FIG. 7B

DETERMINING 3-D FACIAL INFORMATION OF A PATIENT FROM A 2-D FRONTAL IMAGE OF THE PATIENT

CROSS-REFERENCE TO RELATED APPLICATIONS

This patent application claims the priority benefit under 35 U.S.C. § 119(e) of U.S. Provisional Application No. 63/025,822 filed on May 15, 2020, the contents of which are herein incorporated by reference.

BACKGROUND OF THE INVENTION

1. Field of the Invention

The present invention relates to systems and methods for determining masks for patients for use in treating conditions, such as sleep disordered breathing, using positive airway pressure (PAP) therapy. More particularly, the present invention relates to systems and methods for determining such a mask for a patient using three dimensional (3-D) facial information determined from a two dimensional (2-D) frontal image of the patient. The present invention further relates to methods for determining 3-D facial information for a person from a 2-D frontal image of the person.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of a patient. The mask component may be, without limitation, a nasal mask that covers the patient's nose, a nasal cradle that interfaces under a patient's nose, a nasal pillows mask that interfaces with the individual nostrils of a patient, a nasal/oral mask that covers the patient's nose and mouth, or a full face mask that covers the patient's face. Such patient interface devices may also employ other patient contacting components, such as forehead supports, cheek pads, chin pads, silicone frames, and headgear elements. The patient interface device is connected to a gas delivery tube or conduit and interfaces the pressure support device with the airway of the patient, so that a flow of breathing gas can be delivered from the pressure/flow generating device to the airway of the patient.

Current state-of-the art systems for creating or determining a "custom" mask for a patient for use in delivering a flow of a treatment gas to the patient use 3-dimensional scans of the patient which are obtained using expensive 3-D image capturing devices. Alternatively, other methods using multiple images taken at specific locations have been employed to create 3-D models of the patient which are then used in determining a best, or creating a "custom", mask for a patient. The cost of the equipment needed for capturing such 3-D scans and the complexity of the methods needed to successfully obtain accurate data using multiple images limit the applicability of such solutions.

SUMMARY OF THE INVENTION

As one aspect of the present invention, a method of identifying a particular mask for a patient for use in delivering a flow of breathing gas to the patient is provided. The method comprises: receiving a 2-D frontal image of the patient; determining 3-D facial information of the patient from the 2-D frontal image; comparing at least some of the 3-D facial information with dimensional information of a plurality of candidate masks; and determining the particular mask for the patient from a result of the comparison of the at least some of the 3-D facial information and the dimensional information of the plurality of candidate masks.

Receiving the 2-D frontal image of the patient may comprise receiving a 2-D RGB frontal image of the patient. Determining the 3-D facial information of the patient from the 2-D frontal image may comprise analyzing the 2-D frontal image with a trained neural network. Determining the 3-D facial information of the patient from the 2-D frontal image may further comprise determining a 3-D UV position map from the analysis by the trained neural network. Determining the 3-D facial information of the patient from the 2D frontal image may further comprise determining a parametric model of the face of the patient from the 3-D UV position map. The method may further comprise providing the particular mask to the patient. Receiving a 2-D frontal image of the patient may comprise capturing the 2-D frontal image of the patient with a digital imaging device. Capturing the 2-D frontal image of the patient with a digital imaging device may comprise capturing the 2-D frontal image with one of a front-facing camera of a smartphone or a web camera in communication with a computing device.

As another aspect of the present invention, a method of determining 3-D facial information of a patient is provided. The method comprises: receiving a 2-D frontal image of the patient; and determining 3-D facial information of the patient from the 2-D frontal image by analyzing the 2-D frontal image with a trained neural network.

Receiving the 2-D frontal image of the patient may comprise receiving a 2-D RGB image of the patient. Determining the 3-D facial information of the patient from the 2-D frontal image may further comprise determining a 3-D UV position map from the analysis by the trained neural network. Determining the 3-D facial information of the patient from the 2D frontal image may further comprise creating a parametric model from the 3-D UV position map. Receiving a 2-D frontal image of the patient may comprise capturing the 2-D frontal image of the patient with a digital imaging device. Capturing the 2-D frontal image of the patient with a digital imaging device may comprise capturing the 2-D frontal image with one of a front-facing camera of a smartphone or a web camera in communication with a computing device.

As yet a further aspect of the present invention, a system for use in identifying a particular mask for use in delivering a flow of breathing gas to a patient is provided. The system comprises: an input for receiving a 2-D frontal image of the patient; a neural network trained to receive the 2-D frontal image of the patient and determine a 3-D UV position map of the face of the patient; a processing arrangement programmed to: determine 3-D facial information of the face of the patient from the 3-D UV position map, compare at least some of the 3-D facial information with dimensional information of a plurality of candidate masks, and determine the particular mask for the patient from a result of the comparison of the at least some of the 3-D facial information and the dimensional information of the plurality of candidate masks; and an output device in communication with the processing arrangement for providing an indication of the particular mask.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 6A, 7A, 8A and 9A show examples of RGB frontal images captured by a 2-D image capturing apparatus, such as illustrated in FIG. 1;

FIGS. 6B, 7B, 8B and 9B show examples of UV position maps generated by a trained neural network, such as shown in FIG. 1, from the corresponding RGB frontal images of FIGS. 6A, 7A, 8A and 9A; and FIGS. 6C, 7C, 8C and 9C show selected example views of 3-D parametric models, such as generated by the trained neural network shown FIG. 1, from the corresponding UV position maps of FIGS. 6B, 7B, 8B and 9B.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "number" shall mean one or an integer greater than one (i.e., a plurality).

As used herein, the terms "patient" and "user" are used interchangeably to refer to a person whose image is captured/utilized to determine 3-D information thereof, and further to determine therefrom a "custom" mask therefor.

As used herein, a "frontal image" of the face of a patient shall mean an electronic image containing, at minimum the face (e.g., nose, mouth and nearby structures) of the patient positioned looking generally straight-on toward the camera that has been directly captured or otherwise provided with a suitable image capturing device. In example embodiments of the present invention, frontal images in which the face of a patient occupies at least 50% of the image have been utilized. Images wherein the face occupies less than 50% of the image may result in less than optimum results. Additionally, in example embodiments of the present invention, frontal images captured by a device positioned within 50° of a vertical plane bisecting the face of a patient have been employed. In general, images captured with a device positioned as close to the aforementioned vertical plane provide the best results.

As used herein. three-dimensional (3-D) facial information of the patient shall refer to information describing the spacing and/or positioning of landmarks or other points on the face of a patient with respect to each other in three-dimensional space.

Embodiments of the present invention utilize a single two-dimensional (hereinafter "2-D") frontal image of the face of a patient to determine three-dimensional (hereinafter "3-D") facial information of the patient, which then may be employed in comparison with two or three dimensional information of one or more candidate masks to determine a particular mask for suggesting and/or providing to the patient. As previously discussed in the Background section, existing solutions utilize 3-D scanning or multiple images taken at various angles to generate equivalent 3-D facial information.

Figure 1:
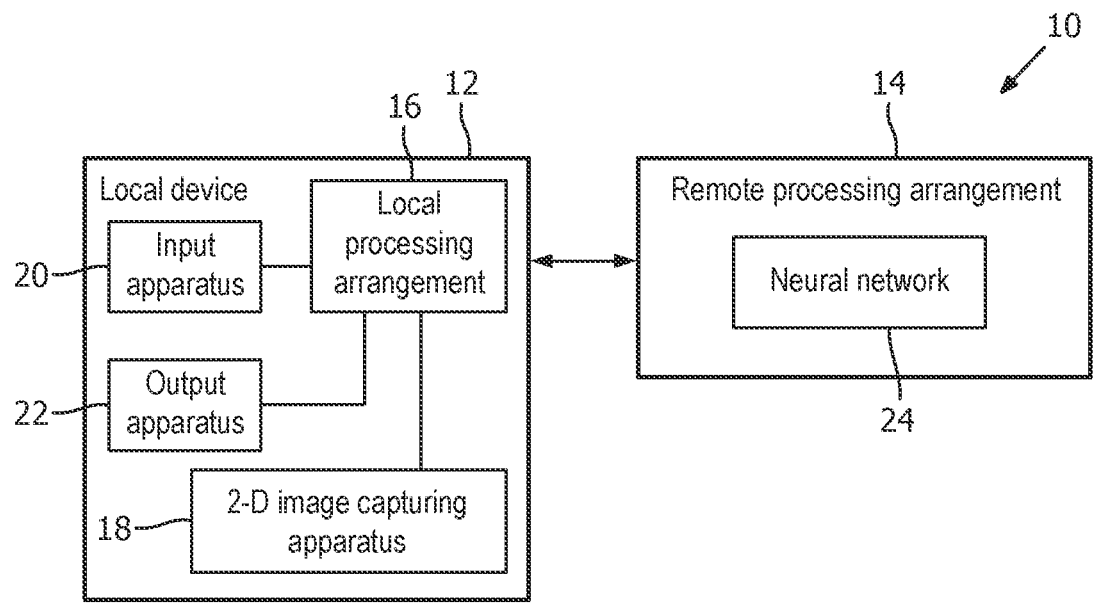
FIG. 1 is a schematic diagram of a system for use in identifying a particular mask for a patient for use in delivering a flow of breathing gas to the patient in accordance with one example embodiment of the present invention.

A schematic diagram of a system 10 for use in identifying a particular mask for a patient, for use in delivering a flow of breathing gas to the patient, in accordance with one example embodiment of the present invention, is shown in FIG. 1. System 10 includes a local device 12 and a remote processing arrangement 14 in bi-directional electronic communication (e.g., via any suitable wired or wireless connection) with local device 12 such that remote processing arrangement 14 can receive input from, and provide output to local device 12. Local device 12 may be a smart phone, laptop or other computer, an electronic kiosk or other suitable arrangement and includes a local processing arrangement 16, as well as a 2-D image capturing apparatus 18, an input apparatus 20, and an output apparatus 22 in electronic communication with local processing arrangement 16. Local processing arrangement 16 comprises a processor, a fixed disk storage device, and a memory module (not numbered).

Local processing arrangement 16 may be, for example and without limitation, a microprocessor (µP) that interfaces with the aforementioned memory module which can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The fixed disk storage device of local processing arrangement 16 has stored therein a number of routines that are executable by local processing arrangement 16.

2-D image capturing apparatus 18 may be any suitable arrangement for electronically capturing, either directly or indirectly, a 2-D image of a person (e.g., without limitation, a front or rear facing camera of a smartphone, a web camera, an electronic scanner, etc.). As discussed below, such 2-D image may be a RGB image (i.e., a color image), a greyscale image, or a black and white image, depending on details of one or more other components of system 10, as discussed further below.

Input apparatus 20 may be any suitable arrangement (e.g., without limitation, a physical keypad or keyboard, a touchscreen, a microphone, a video camera, etc.) for providing at least minimal input to local device 12, and more particularly, local processing arrangement 16, without varying from the scope of the present invention. Output apparatus 22 may be any suitable arrangement for providing output from local processing arrangement 16 and/or local device 12 in general. More particularly, output apparatus 22 may be any arrangement suitable for providing an indication of a particular mask or for providing an actual particular mask to a user. For example, as discussed further below, system 10 determines a particular mask for a patient and may provide, dependent on a particular application, information regarding the particular mask determined (e.g., without limitation, model, sizing, how to obtain, etc.) and or may actually provide the particular mask determined. Accordingly, output apparatus 22 may be any of a multitude of suitable arrangements (e.g., without limitation, a display screen, a speaker, a selectably accessible compartment or compartments housing a number of masks) without varying form the scope of the present invention.

Figure 3:
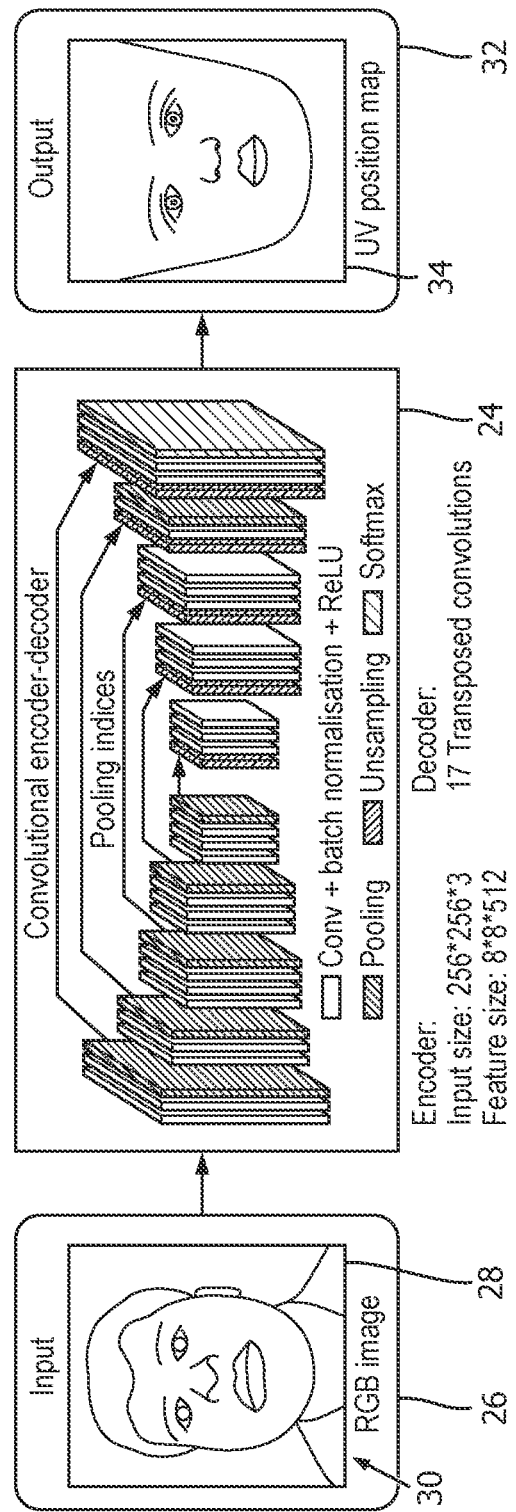
FIG. 3 is an example representation of operation of a neural network in accordance with one example embodiment of the present invention showing an example input and corresponding output thereof.

Remote processing arrangement 14 is a cloud-based processing arrangement comprising in-whole or in-part a trainable neural network 24 of commonly known architecture. More particularly, neural network 24 has been trained to produce a 3-D position map of the face of a user solely from a single 2-D frontal image of the user provided as input to neural network 24. As used herein, a "trained neural network" is a neural network that has been trained, e.g., via conventional techniques, to produce a 3-D positon map of a face of a user/patient from a 2-D frontal image of the user/patient. In one example embodiment of the present invention, such as generally exemplified in FIG. 3, neural network 24 was trained to receive as input 26 a 2-D RGB frontal image 28 of the face of a user 30 and provide an output 32 in the form of a UV position map 34. As used herein, a "UV position map" is a map containing depth information of all of the pixels of the face (or relevant portion thereof) of a user (e.g., user 30 in FIG. 3). Such training of neural network 24 was carried out by providing UV position maps, obtained from a diverse sampling of approximately 3000 using conventional 3-D scanning equipment and techniques, to neural network 24. Neural network 24 was also provided with 2-D frontal images of each of the persons that were extracted from each of the aforementioned UV position maps. From such training, neural network 24 was effectively taught to create a 3-D UV position map (such as map 34 in FIG. 3) as output 32 solely from a 2-D RGB frontal image (such as frontal image 28 of FIG. 3) provided as input 26 to neural network 24.

Figure 4:
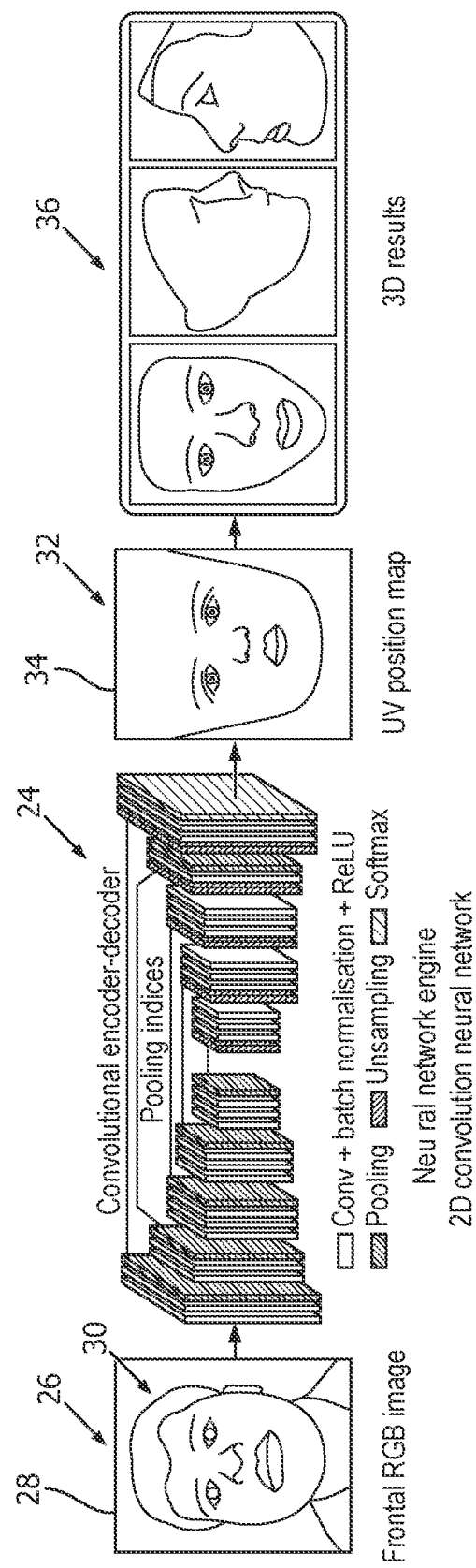
FIG. 4 is an example representation of operation of a neural network similar to FIG. 3 but further showing an example of the output of the neural network translated into a 3-D form.

As shown in FIG. 4, such 3-D UV position map 34, can then be translated into a 3-D parametric model 36 (three 2-D views thereof are shown in the Example of FIG. 4) for use in comparing with 3-D dimensional information of one or more candidate masks in determining a recommended mask for the user. Although shown using 2-D RGB images, it is to be appreciated that 2-D greyscale images could also be employed by similarly training neural 24 using similar training materials except using materials in greyscale instead of RGB.

Figure 2:
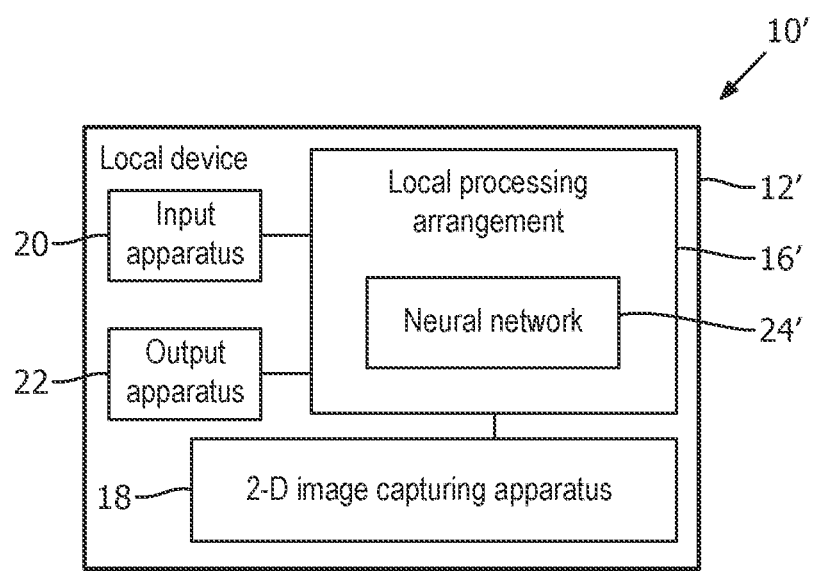
FIG. 2 is a schematic diagram of another system for use in identifying a particular mask for a patient for use in delivering a flow of breathing gas to the patient in accordance with one example embodiment of the present invention.

A schematic diagram of another system 10' for use in identifying a particular mask for a patient, for use in delivering a flow of breathing gas to the patient, in accordance with another example embodiment of the present invention is shown in FIG. 2. System 10' is similar to system 10, previously discussed, except system 10' is contained wholly within a local device 12'. More particularly, local device 12' is of similar arrangement as local device 12 except local device 12' includes a neural network 24' (similar to neural network 24, previously discussed) provided as, or as a portion of a local processing arrangement 16'.

Figure 5:
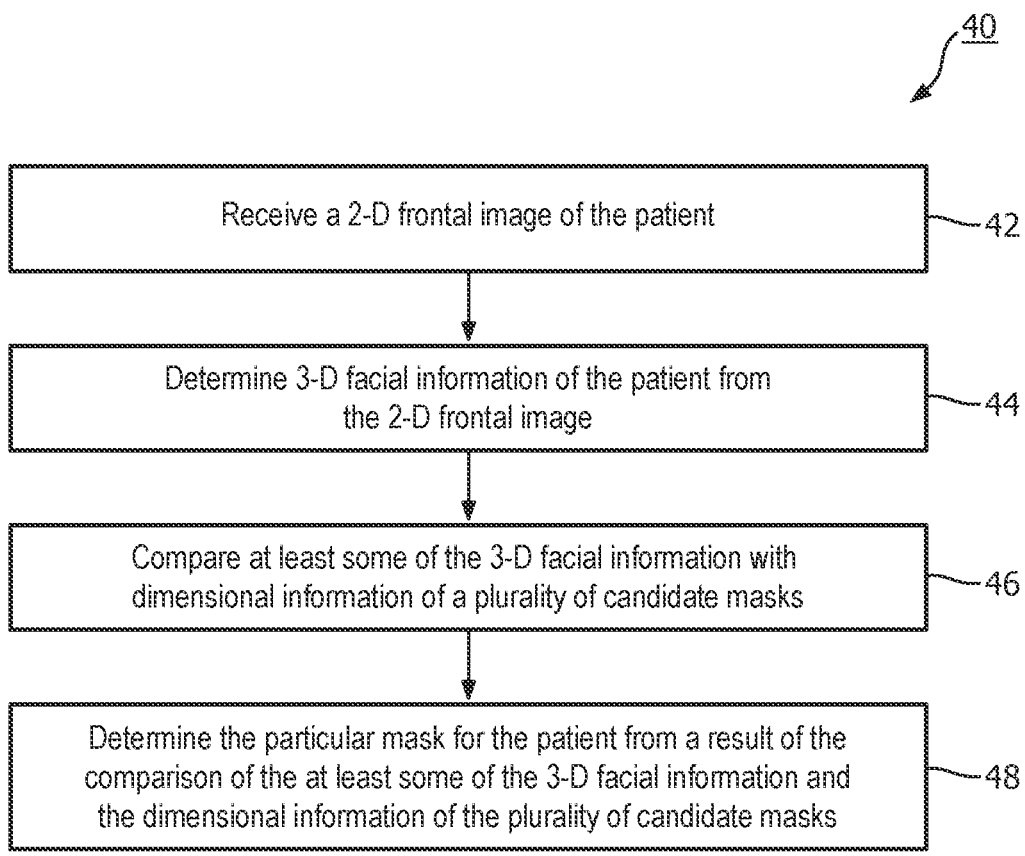
FIG. 5 is a flowchart of a method in accordance with one example embodiment of the present invention.
Figures 8A, 8C:
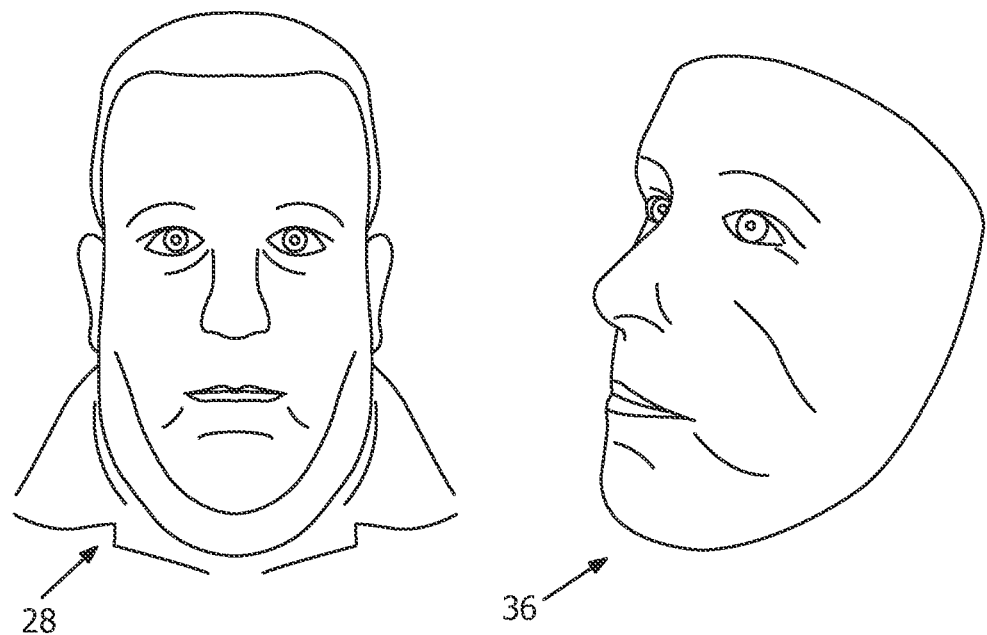
Figure 8B:
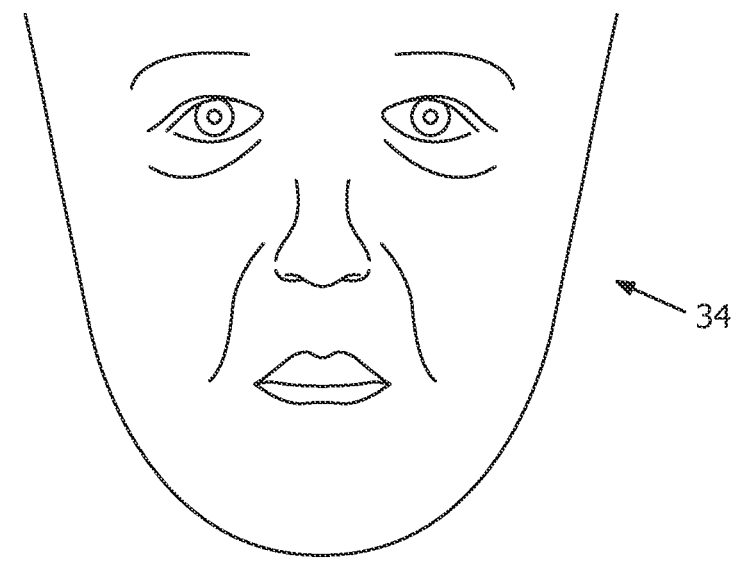
Figures 9A, 9C:
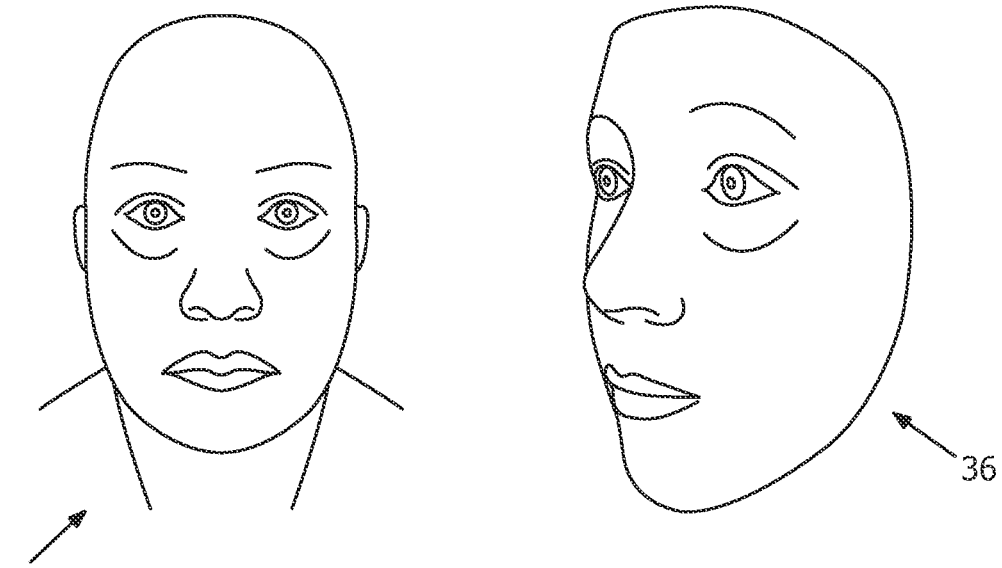
Figure 9B:
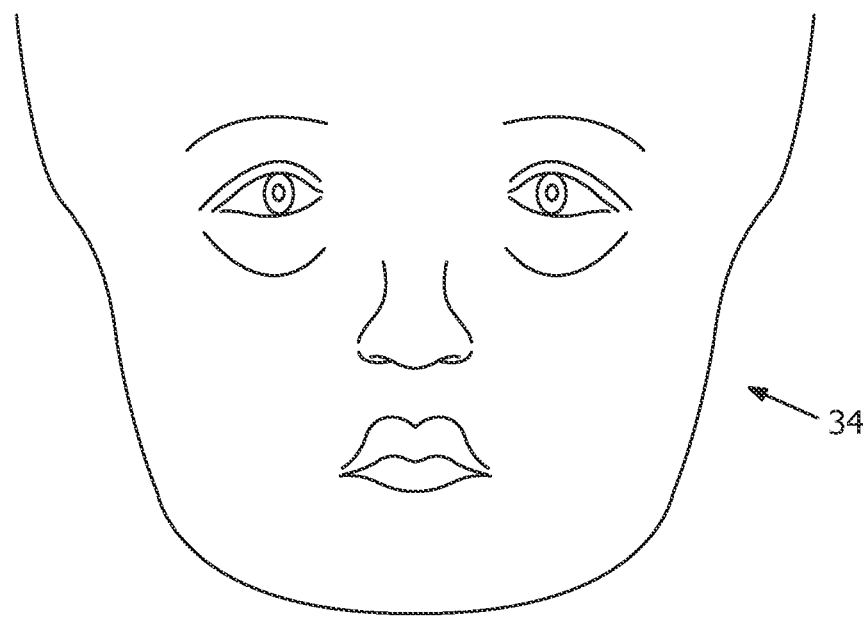

Having thus described some example systems 10, 10' in accordance with some example embodiments of the present invention, along with details and general operation of components thereof, an example method 40 carried out via either of such systems 10, 10' (or any other suitable arrangement) of identifying a particular mask for a patient for use in delivering a flow of breathing gas to the patient, in accordance with one example embodiment of the present invention will not be described with reference to FIG. 5.

Method 40 begins at 42 wherein a 2-D frontal image of the patient is received. In the example systems 10 and 10' of FIGS. 1 and 2, such 2-D frontal image may be an RGB image, captured using 2-D image capturing apparatus 18, that is provided to, and received by trained neural network 24 or 24' for processing thereby.

Next, at 44, 3-D facial information of the patient is determined from the 2-D frontal image. In the example systems 10 and 10' of FIGS. 1 and 2, such determination is carried out by trained neural network 24 or 24' that receives the 2-D RGB frontal image and determines/produces as an output therefrom a 3-D UV position map. A parametric model of the face of the patient may be determined from the 3-D UV position map.

Next, at 46, at least some of the 3-D facial information is compared with dimensional information of a plurality of candidate masks. In the example systems 10 and 10' of FIGS. 1 and 2, such comparison may be carried out by neural networks 24 or 24' or local processing arrangements 16 or 16' using rulesets or other methodology such as generally known in the art for finding a best 3-D fit between the interfacing portions of the mask and the face of the patient/user.

Finally, method 40 generally concludes at 48, wherein the particular mask for the patient is determined from a result of the comparison carried out at 46 of at least some of the 3-D facial information and the dimensional information of the plurality of candidate masks. Such determination of the of the particular mask for the patient/user may include providing information identifying the particular mask (e.g., without limitation, style, model #, size, etc.) to the user and/or providing the actual particular mask to the patient. In the example systems 10 and 10' of FIGS. 1 and 2, such providing of the information identifying the particular mask and/or the actual particular mask to the patient may be carried out using output apparatus 22 such as previously described.

FIGS. 6A-6C, 7A-7C, 8A-8C and 9A-9C, show examples of RGB frontal images 28 (FIGS. 6A, 7A, 8A and 9A) provided to trained neural network 24 of system 10; UV position maps 34 (FIGS. 6B, 7B, 8B and 9B) generated by trained neural network 24 from the corresponding frontal image 28; and example views of 3-D parametric models 36 (FIGS. 6C, 7C, 8C and 9C) further generated by trained neural network 24 from the aforementioned generated UV position maps 34.

From the foregoing, it is thus to be appreciated that embodiments of the present invention provide solutions for identifying/providing a "custom" mask for particular users/patients from a readily obtainable basic 2-D frontal image of the patient.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of identifying a particular mask for a patient for use in delivering a flow of breathing gas to the patient, the method comprising:
   receiving, with a local device, a 2-D frontal image of the patient, wherein the local device includes:
      a local processing arrangement, and
      an output apparatus in communication with the local processing arrangement;
   communicating the 2-D frontal image to a cloud-based, remote processing arrangement comprising:
      a neural network trained to receive the 2-D frontal image of the patient from the local device and determine a 3-D UV position map of the face of the patient;
   determining, with the remote processing arrangement, 3-D facial information of the patient from the 2-D frontal image;
   comparing at least some of the 3-D facial information with dimensional information of a plurality of candidate masks;
   determining the particular mask for the patient from a result of the comparison of the at least some of the 3-D facial information and the dimensional information of the plurality of candidate masks; and
   outputting an indication of the particular mask, wherein only the remote processing arrangement is programmed to:
      determine the 3-D facial information of the face of the patient from the 3-D UV position map,
      compare the at least some of the 3-D facial information with dimensional information of a plurality of candidate masks, and
      determine the particular mask for the patient from a result of the comparison of the at least some of the 3-D facial information and the dimensional information of the plurality of candidate masks.

2. The method of claim 1, wherein receiving the 2-D frontal image of the patient comprises receiving a 2-D RGB frontal image of the patient.

3. The method of claim 1, wherein determining the 3-D facial information of the patient from the 2-D frontal image comprises analyzing the 2-D frontal image with a trained neural network of the remote processing arrangement.

4. The method of claim 3, wherein determining the 3-D facial information of the patient from the 2-D frontal image further comprises determining a 3-D UV position map from the analysis by the trained neural network.

5. The method of claim 4, wherein determining the 3-D facial information of the patient from the 2D frontal image further comprises determining a parametric model of the face of the patient from the 3-D UV position map.

6. The method of claim 1, further comprising providing the particular mask to the patient.

7. The method of claim 1, wherein receiving the 2-D frontal image of the patient comprises capturing the 2-D frontal image of the patient with a digital imaging device.

8. The method of claim 7, wherein capturing the 2-D frontal image of the patient with a digital imaging device comprises capturing the 2-D frontal image with one of a front-facing camera of a smartphone or a web camera in communication with a computing device.

9. A system for use in identifying a particular mask for use in delivering a flow of breathing gas to a patient, the system comprising:
  a local device for receiving a 2-D frontal image of the patient, the local device comprising:
    a local processing arrangement; and
    an output apparatus in communication with the local processing arrangement;
  a cloud-based, remote processing arrangement comprising:
    a neural network trained to receive the 2-D frontal image of the patient from the local device and determine a 3-D UV position map of the face of the patient,
  wherein the local processing arrangement and/or the remote processing arrangement is programmed to:
    determine 3-D facial information of the face of the patient from the 3-D UV position map,
    compare at least some of the 3-D facial information with dimensional information of a plurality of candidate masks, and
    determine the particular mask for the patient from a result of the comparison of the at least some of the 3-D facial information and the dimensional information of the plurality of candidate masks, and
  wherein the output apparatus is structured to provide an indication of the particular mask, and
  wherein only the remote processing arrangement is programmed to:
    determine the 3-D facial information of the face of the patient from the 3-D UV position map,
    compare the at least some of the 3-D facial information with dimensional information of a plurality of candidate masks, and
    determine the particular mask for the patient from a result of the comparison of the at least some of the 3-D facial information and the dimensional information of the plurality of candidate masks.

10. The system of claim 9, further comprising a 2-D image capturing apparatus structured to capture the 2-D frontal image of the patient.

11. The system of claim 10, wherein the 2-D image capturing apparatus comprises a front-facing camera of a smartphone or a web camera in communication with a computing device.

12. A system for use in identifying a particular mask for use in delivering a flow of breathing gas to a patient, the system comprising:
  a local device for receiving a 2-D frontal image of the patient, the local device comprising:
    a local processing arrangement; and
    an output apparatus in communication with the local processing arrangement;
  a cloud-based, remote processing arrangement comprising:
    a neural network trained to receive the 2-D frontal image of the patient from the local device and determine a 3-D UV position map of the face of the patient,
  wherein the local processing arrangement and/or the remote processing arrangement is programmed to:
    determine 3-D facial information of the face of the patient from the 3-D UV position map,
    compare at least some of the 3-D facial information with dimensional information of a plurality of candidate masks, and
    determine the particular mask for the patient from a result of the comparison of the at least some of the 3-D facial information and the dimensional information of the plurality of candidate masks, and
  wherein the output apparatus is structured to provide an indication of the particular mask,
  wherein only the local processing arrangement is programmed to:
    determine the 3-D facial information of the face of the patient from the 3-D UV position map,
    compare the at least some of the 3-D facial information with dimensional information of a plurality of candidate masks, and
    determine the particular mask for the patient from a result of the comparison of the at least some of the 3-D facial information and the dimensional information of the plurality of candidate masks.

* * * * *